United States Patent
Fearns et al.

(10) Patent No.: US 10,632,817 B2
(45) Date of Patent: Apr. 28, 2020

(54) METHOD OF OPERATING AN ENVIRONMENTAL CONTROL SYSTEM

(71) Applicant: FORD GLOBAL TECHNOLOGIES, LLC, Dearborn, MI (US)

(72) Inventors: Liberty Fearns, East Ham (GB); Felix Noller, London (GB)

(73) Assignee: Ford Global Technologies, LLC, Dearborn, MI (US)

( * ) Notice: Subject to any disclaimer, the term of this patent is extended or adjusted under 35 U.S.C. 154(b) by 314 days.

(21) Appl. No.: 15/467,368

(22) Filed: Mar. 23, 2017

(65) Prior Publication Data
US 2017/0282684 A1    Oct. 5, 2017

(30) Foreign Application Priority Data
Mar. 30, 2016 (GB) .................... 1605340.7

(51) Int. Cl.
| | | |
|---|---|---|
| B60H 1/00 | (2006.01) | |
| A61B 5/18 | (2006.01) | |
| A61B 5/01 | (2006.01) | |
| A61B 5/024 | (2006.01) | |
| B60Q 3/80 | (2017.01) | |
| A61M 21/00 | (2006.01) | |
| B60H 3/00 | (2006.01) | |
| A61B 5/00 | (2006.01) | |
| A61B 5/11 | (2006.01) | |

(52) U.S. Cl.
CPC .......... *B60H 1/00742* (2013.01); *A61B 5/01* (2013.01); *A61B 5/024* (2013.01); *A61B 5/18* (2013.01); *A61M 21/00* (2013.01); *B60H 3/0035* (2013.01); *B60Q 3/80* (2017.02); *A61B 5/1114* (2013.01); *A61B 5/4809* (2013.01); *A61B 5/4812* (2013.01); *A61M 2021/0083* (2013.01)

(58) Field of Classification Search
None
See application file for complete search history.

(56) References Cited

U.S. PATENT DOCUMENTS 7,248,997 B2 *  7/2007  Nagai ................. A61B 5/18
                                                        702/182
8,743,193 B2 *  6/2014  Bogner ............... G08B 21/06
                                                        348/143
(Continued)

FOREIGN PATENT DOCUMENTS

| JP | 2013012029 A | 1/2013 |
|---|---|---|
| WO | 2008091965 A1 | 7/2008 |
| WO | 2012173090 A1 | 12/2012 |

OTHER PUBLICATIONS

Combined Search and Examination Report in Patent Application No. GB1605340.7 dated Sep. 26, 2016.
(Continued)

*Primary Examiner* — Peter D Nolan
(74) *Attorney, Agent, or Firm* — Gregory P. Brown; Brooks Kushman P.C.

(57) ABSTRACT

One or more environmental control systems of a vehicle are automatically operated. A position of an occupant of the vehicle in their circadian cycle is determined. The operation of one or more of the environmental control systems is controlled to compensate for or adjust the position of the occupant in their circadian cycle.

16 Claims, 3 Drawing Sheets

(56) References Cited

U.S. PATENT DOCUMENTS

| | | | | |
|---|---|---|---|---|
| 9,024,764 | B2* | 5/2015 | Chang | A61B 5/01 340/449 |
| 9,384,421 | B2* | 7/2016 | Offenhaeuser | G06K 9/6255 |
| 9,456,770 | B2* | 10/2016 | Fujita | A61B 5/11 |
| 9,820,687 | B2* | 11/2017 | Wulf | A61B 5/18 |
| 9,848,813 | B2* | 12/2017 | Kronberg | A61B 5/18 |
| 2004/0044291 | A1 | 3/2004 | Yasushi et al. | |
| 2005/0246134 | A1* | 11/2005 | Nagai | A61B 5/18 702/182 |
| 2008/0180235 | A1* | 7/2008 | Chang | A61B 5/01 340/449 |
| 2012/0212353 | A1* | 8/2012 | Fung | B60K 28/06 340/905 |
| 2013/0119891 | A1* | 5/2013 | Herremans | H05B 33/0857 315/293 |
| 2013/0162797 | A1* | 6/2013 | Bogner | G08B 21/06 348/78 |
| 2015/0110402 | A1* | 4/2015 | Offenhaeuser | G06K 9/6255 382/190 |
| 2015/0216466 | A1* | 8/2015 | Kronberg | A61B 5/18 702/19 |
| 2015/0258996 | A1* | 9/2015 | Victor | G09B 19/16 340/576 |
| 2015/0327803 | A1* | 11/2015 | Fujita | A61B 5/11 340/576 |
| 2015/0351681 | A1* | 12/2015 | Lee | A61B 5/4806 600/595 |
| 2016/0023662 | A1* | 1/2016 | Wulf | B60W 40/08 340/576 |
| 2016/0071393 | A1* | 3/2016 | Kaplan | A61B 5/6831 340/539.12 |
| 2017/0150930 | A1* | 6/2017 | Shikii | A61B 5/0261 |
| 2017/0164883 | A1* | 6/2017 | Wulf | A61B 5/18 |
| 2017/0313190 | A1* | 11/2017 | Shimada | A61B 5/18 |
| 2018/0330811 | A1* | 11/2018 | Macary | G06Q 10/0639 |

OTHER PUBLICATIONS

Combined Search and Examination Report in Patent Application No. GB1617344.5 dated Nov. 4, 2016.

* cited by examiner

METHOD OF OPERATING AN ENVIRONMENTAL CONTROL SYSTEM

CROSS-REFERENCE TO RELATED APPLICATIONS

This application claims foreign priority benefits under 35 U.S.C. § 119(a)-(d) to GB Application 1605340.7 filed Mar. 30, 2016, which is hereby incorporated by reference in its entirety.

TECHNICAL FIELD

The present disclosure relates to a method of operating one or more environmental control systems of a motor vehicle and is particularly, although not exclusively, concerned with a method of operating one or more environmental control systems in order to regulate a circadian rhythm of an occupant of the vehicle.

BACKGROUND

Many processes that occur in the human body operate according to a regular cycle of approximately 24 hours known as the circadian rhythm or circadian cycle. In particular, a person's sleep-wake cycle typically occurs over a 24 hour period during which their sleep requirement gradually increases until the person sleeps and reduces their sleep requirement back to a base level. Similarly, a person's core body temperature varies in a cycle over the same approximate 24 hour period.

Although the processes naturally occur over an approximately constant 24 hour period, a person's circadian rhythm can be influenced by external factors, that may extend the cycle, e.g., by keeping the person awake longer than normal, or shorten the cycle, e.g., by increasing the person's sleep requirement. Alternatively, the external factors may change the rate that a person progresses through their circadian cycle or change a person's position on their circadian cycle making them more awake or more ready for sleep than they would normally be at that time of day or point in their circadian rhythm. Changes to the person's circadian cycle or the position of a person on their circadian rhythm may affect each of the natural processes that occur in time with the circadian rhythm.

SUMMARY

According to an aspect of the present disclosure, there is provided a method for operating one or more environmental control systems of a motor vehicle, the method comprising:
determining a position of an occupant of the vehicle in their circadian cycle, e.g. their sleep-wake cycle; and
controlling the operation of one or more of the environmental control systems to compensate for or adjust the position of the occupant in their circadian cycle.

A person's circadian cycle or circadian rhythm may be a period, often of approximately 24 hours, over which many natural processes of the body operate, such as becoming tired and sleeping, e.g., sleep-wake cycle, and hormone production.

The method may comprise determining a core body temperature of the occupant. The position of the occupant in their circadian cycle may be determined at least partially based on their core body temperature.

The core body temperature of the occupant may be determined based on a skin temperature of the occupant. The skin temperature of the occupant may be determined using an infra-red thermometer provided on the vehicle.

The method may comprise storing the core body temperature of the occupant in a memory associated with the controller. The method may further comprise associating the stored temperature with the time of day at which the temperature was determined. The method may further comprise processing the stored temperatures to determine a standard circadian cycle of the occupant, e.g., a model of expected or usual core body temperature of the occupant according to the time of day.

The method may comprise determining a sleep requirement of the occupant. The sleep requirement of the occupant may be determined at least partially based on their core body temperature. The standard circadian cycle of the occupant may comprise a model of expected or usual sleep requirement of the occupant according to their core body temperature and/or time of day. The sleep requirement of the occupant may be at least partially determined by referring the core body temperature of the occupant to the occupant's standard circadian cycle.

The environmental control systems may be controlled in order to adjust the occupant's position on their circadian cycle to be substantially aligned with or closer to the occupant's standard circadian cycle, e.g., such that the occupant's core body temperature or sleep requirement is substantially equal to or closer to the usual or expected value for the current time of day, according to their standard circadian cycle.

If the occupant's sleep requirement is high for the current time of day compared to their standard circadian cycle, the environmental control systems may be controlled to waken the occupant. For example, the brightness of illumination providing by a lighting system may be increased or the frequency of light emitted may be increased, an air conditioning system may be operated to reduce the temperature of the vehicle interior and/or the volume, tempo, equalization and/or style of media being played by a media system be adjusted.

The environmental control systems may comprise a lighting system configured to illuminate the interior of the vehicle. The method may comprise controlling the color and/or intensity of the illumination provided according to the occupant's position on their circadian cycle, e.g., compared to their standard circadian cycle. For example, if the occupant is at a later point in their circadian cycle than usual for the time of day, e.g., is ahead of their standard circadian cycle, and/or has a greater than usual sleep requirement, the lighting system may be adjusted to provide light with a higher frequency and/or intensity. Similarly, if the occupant is at an earlier point in their circadian cycle than usual for the time of day, e.g., is behind their standard circadian cycle, and/or has a lower than usual sleep requirement, the lighting system may be adjusted to provide light with a lower frequency and/or intensity.

Additionally or alternatively, the environmental control systems may comprise a climate control system, such as an air conditioning and/or heating system. The method may comprise controlling the climate control system to regulate an interior temperature of the vehicle according to the occupant's position on their circadian cycle. For example, if the occupant is at a later point in their circadian cycle than usual for the time of day, e.g., compared to their standard circadian cycle, and/or has a greater sleep requirement, the climate control system may reduce the interior temperature of the vehicle. Similarly, if the occupant is at an earlier point in their circadian cycle than usual for the time of day, e.g., compared to their standard circadian cycle, and/or has a lower sleep requirement, the climate control system may increase the interior temperature of the vehicle.

Additionally or alternatively again, the environmental control systems may comprise a media system. The method may comprise controlling the volume, tempo and/or equalization of media played by the media system according to the occupant's position on their circadian cycle. For example, if the occupant is at an earlier point in their circadian cycle than usual for the time of day, e.g., compared to their standard circadian cycle, and/or has a lower sleep requirement, the media system may reduce the volume and/or tempo of media being played and/or may select media with a lower tempo to be played. Similarly, if the occupant is at a later point in their circadian cycle than usual for the time of day, e.g., compared to their standard circadian cycle, and/or has a higher sleep requirement, the media system may increase the volume and/or tempo of media being played and/or may select media with a higher tempo to be played.

Additionally or alternatively again, the environmental control systems may comprise an air quality system, configured to control the oxygen level within the interior of the vehicle. The method may comprise, controlling the air quality system to adjust the oxygen level according to the occupant's position on their circadian cycle, e.g. to increase the level of oxygen within the interior of the vehicle.

The method may further comprise determining a heart rate of the occupant. The position of the occupant on their circadian cycle may be determined at least partially based on the heart rate of the occupant.

The method may comprise communicating with an activity monitor to receive activity information. The activity monitor may be configured to be worn or carried by the occupant. The activity monitor may be configured to monitor activities performed by the occupant. For example, the activity information may comprise heart rate information and/or information relating to a sleep cycle of the occupant. The method may further comprise determining a standard circadian cycle of the occupant based at least partially on the activity information.

The method may comprise receiving calendar information relating to an appointment attended or planned by the occupant. For example, calendar information may be received from a portable computing device, smart phone of the occupant or via a calendar accessible online or over a computer network. The method may further comprise determining a standard circadian cycle of the occupant based at least partially on the calendar information.

The method may comprise determining the occupant's expected position on their circadian cycle at the time of a planned appointment. The method may further comprise determining the occupant's expected sleep requirement at the time of the planned appointment.

The method may comprise controlling the operation of one or more of the environmental control systems to adjust the occupant's expected position on their circadian cycle at the time of the planned appointment. For example, if the occupant's sleep requirement is expected to be too high.

The method may comprise determining a desired position of the occupant on their circadian cycle and/or a desired maximum sleep requirement of the user for attending the planned appointment. The environmental control systems may be controlled to adjust the position of the occupant on their circadian cycle and/or their sleep requirement such that the positon and/or sleep requirement is substantially equal to the desired positon or value at the time of the planned appointment.

The method may further comprise determining an alternative time to perform the planned appointment when the occupant is expected to be at a desired position on their circadian cycle. For example, when the occupant's sleep requirement is expected to be lower.

The method may comprise determining a time zone difference expected to be experienced by the occupant based on a planned appointment. The method may further comprise determining a desired circadian rhythm according to the time zone difference. The method may further comprise controlling the operation of one or more of the environmental control systems to adjust the occupant's position on their circadian cycle to be substantially aligned with the desired circadian rhythm.

The expected time zone difference may be determined by comparing the time zone of a location of the planned appointment and the time zone at the current location of the vehicle. Alternatively, the time zone difference resulting from a planned appointment, e.g., a travel appointment, may be determined.

The method may further comprise determining a time zone difference experienced by the occupant based on a previously attended appointment. The method may comprise determining a jet lag of the occupant according to the time zone difference. The method may further comprise controlling the operation of one or more of the environmental control systems to adjust the occupant's position on their circadian cycle to be substantially aligned with the occupant's standard circadian cycle, e.g., in order to counteract the effects of jet lag.

The time zone difference may be determined by comparing the time zone of a location of the previously attended appointment and the time zone at the current location of the vehicle. Alternatively, the time zone difference that may have resulted from the previously attended appointment occupant may be determined, for example if the appointment was a travel appointment According to another aspect of the present disclosure, there is provided a motor vehicle, comprising: one or more environmental control systems; and a controller configured to perform the method according a previously mentioned aspect of the disclosure.

The vehicle may further comprise a thermometer configured to determine a temperature of the occupant, e.g., a skin temperature of the occupant. The thermometer may be an infra-red thermometer configured to determine the temperature at or close to a central region of the occupant's forehead, or a temple region of the occupant's head.

According to another aspect of the present disclosure, there is provided an illumination system for a motor vehicle, the system comprising:

a thermometer configured to measure a temperature of an occupant of the motor vehicle;

one or more light sources; and a controller configured to:

determine a core body temperature of the occupant based on measurement from the thermometer;

determine a sleep requirement of the occupant based on the core body temperature;

control the illumination provided by the one or more light sources according to the sleep requirement of the occupant.

To avoid unnecessary duplication of effort and repetition of text in the specification, certain features are described in relation to only one or several aspects or arrangements of the invention. However, it is to be understood that, where it is technically possible, features described in relation to any aspect or arrangement of the invention may also be used with any other aspect or arrangement of the invention.

For a better understanding of the present invention, and to show more clearly how it may be carried into effect, reference will now be made, by way of example, to the accompanying drawings, in which:

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
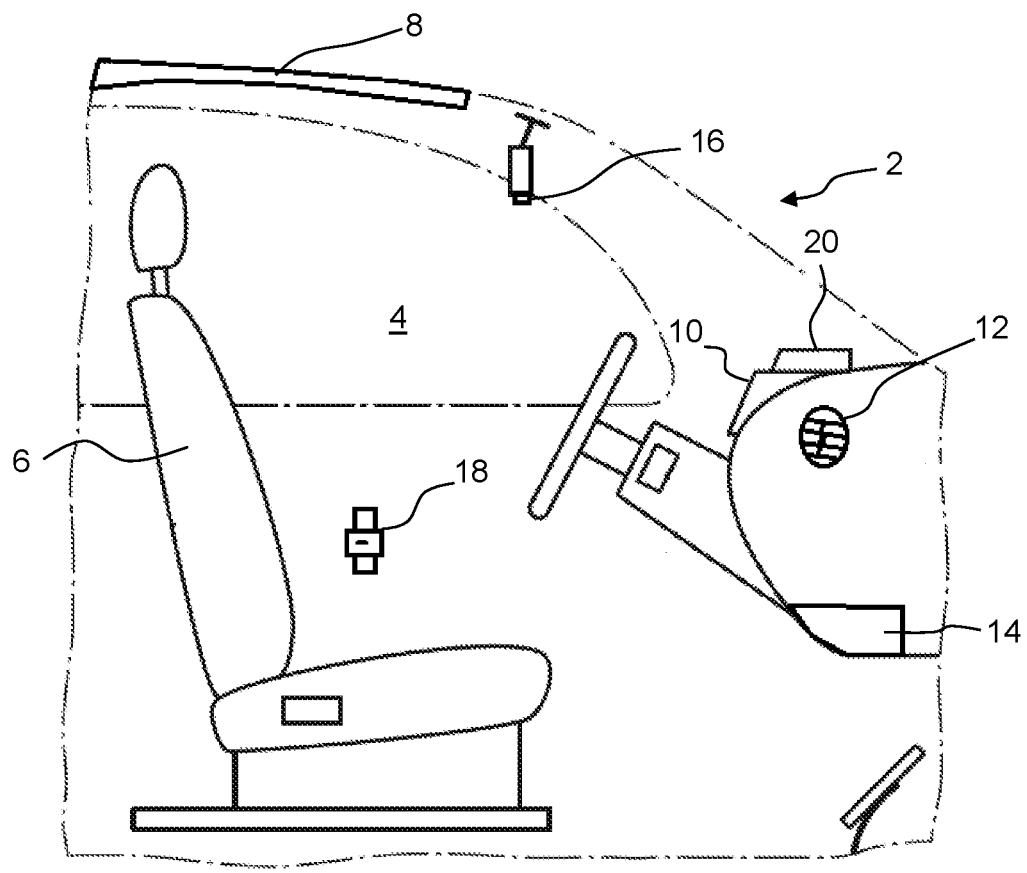
FIG. 1 is a side view of an interior of a vehicle according to arrangements of the present disclosure.

With reference to FIG. 1, a vehicle 2, such as a motor vehicle comprises an interior 4, comprising one or more seats 6 for occupants of the vehicle. The vehicle further comprises one or more environmental control systems configured to control the environment within the vehicle interior. For example, as shown in FIG. 1, the vehicle may comprise a lighting system 8, configured to provide illumination within the vehicle interior 4; a media system 10, configured to allow the playback of media such as music and/or video using speakers and/or display screens provided in the vehicle; a climate control system 12, such as an air conditioning and/or heating system, configured to regulate the temperature within the vehicle interior; and an air quality system 14, configured to regulate the quality of air within the vehicle interior. For example, the air quality system 14 may regulate the amount of carbon dioxide and/or oxygen present within the vehicle interior. The vehicle may further comprise a controller 20 configured to control the operation of the one or more environmental control systems.

The vehicle 2 may comprise a temperature sensor 16, such as an infra-red temperature sensor, configured to determine a temperature of an occupant of the vehicle. The occupant may be a driver of the vehicle. Additionally or alternatively, the temperature sensor 16 may be configured to determine temperatures of one or more passengers in the vehicle. In the arrangement depicted in FIG. 1, the temperature sensor 16 is an infra-red temperature sensor configured to determine a temperature, e.g., a skin temperature, at a central region of the occupant's forehead, or the temple region of the occupant's head.

The temperature sensor may be remote, e.g., spaced apart, from the occupant. For example, as shown in FIG. 1, the temperature sensor may be provided on, e.g. integral with, a rear view mirror of the vehicle. Alternatively, the temperature sensor 16 may be provided on a steering wheel, dash board or ceiling of the vehicle or in any other location in the vehicle where it is able to measure the occupant's temperature. In some arrangements, more than one temperature sensor may be provided on the vehicle 2.

The temperature sensor 16 may be configured to determine a temperature at a single location at the central region of the occupant's forehead, or the temple region of the occupant's head. Alternatively, the temperature sensor 16 may be configured to determine a maximum or average temperature of the occupant's forehead, e.g., within the central region, and the temple region of the occupant's head.

The vehicle 2 may further comprise a camera (not shown) configured to capture an image of the occupant of the vehicle. The camera, or a controller associated with the camera, may be configured to determine the location of the occupant's forehead and/or a temple region of the occupant's head. The position and/or orientation of the temperature sensor 16 may be adjusted to allow the temperature of at or close to a central region of the occupant's forehead, or the temple region of the occupant's head to be measured.

In some arrangements, the temperature sensor 16 may comprise an infra-red camera. The infra-red camera may be configured to capture an image of an occupant of the vehicle and the infra-red camera, or a controller associated with the infra-red camera, may determine the location of the occupant's forehead and/or a temple region of the occupant's head in the image. The controller may also optionally be associated with another camera, such as described above, e.g., a non-infra-red camera, to help determine the location of the occupant's forehead and/or temple region. The infra-red camera and/or controller may determine the temperature at or close to a central region of the occupant's forehead, or the temple region of the occupant's head by referring to the image captured by the infra-red camera.

The temperatures at the central region of a person's forehead and at the temple region of the head provide good indications of a person's core body temperature and hence, the temperature sensor 16 may be configured to allow a core body temperature of the occupant to be determined.

Figure 2:
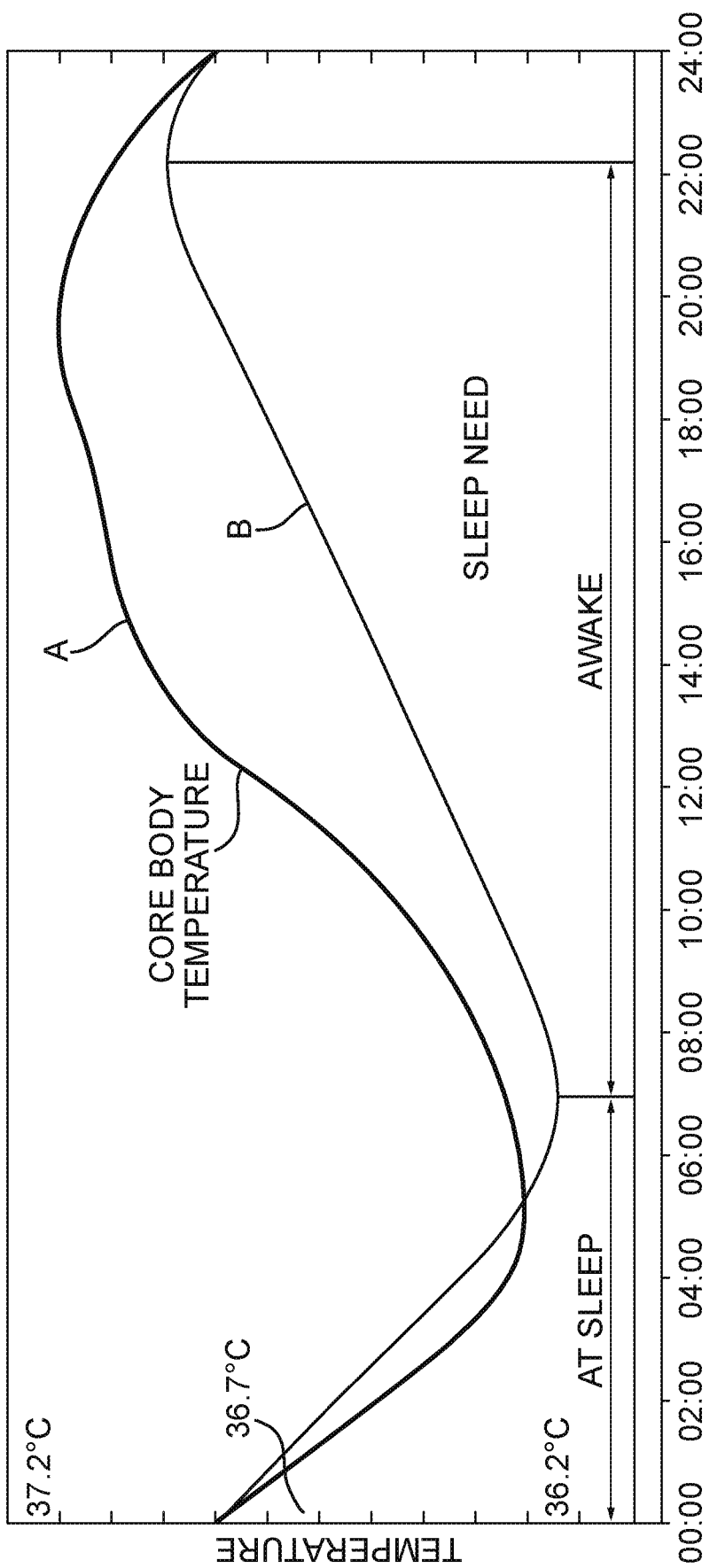
FIG. 2 shows a graph showing the variations in sleep requirement and core body temperature of a person over their circadian cycle.

With reference to FIG. 2, a person's core body temperature may vary during the person's circadian cycle in a regular pattern. In FIG. 2, line A indicates core body temperature. As mentioned above, other natural processes of the body may occur according to the same rhythm. For example, line B indicates the sleep requirement of the person. As shown, core body temperature may be lowest when sleep requirement is lowest and core body temperature may increase as sleep requirement increases.

The position of a person on their circadian cycle may indicate the state of each of the bodily processes governed by the circadian cycle. Hence, by determining a person's core body temperature, and comparing it to their natural cycle of core body temperature over their standard circadian cycle, the position of the person on their circadian cycle can be determined and thereby the state of the other processes governed by the circadian cycle may be determined. For example, a sleep requirement of the person may be determined. The sleep requirement of the person may indicate how tired or awake the person is feeling.

Figure 3:
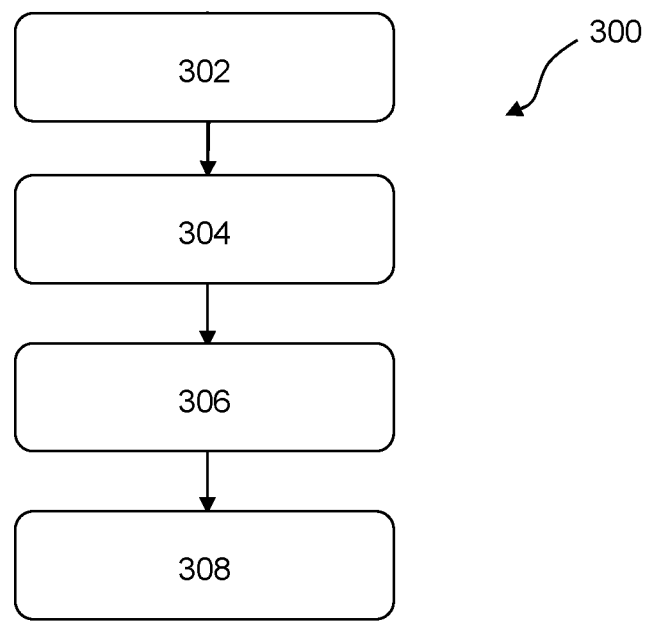
FIG. 3 shows a method of determining a standard circadian cycle of a person according to arrangements of the present disclosure.

With reference to FIG. 3, a method 300 of determining a standard circadian cycle of an occupant of the vehicle 2, according to arrangements of the present disclosure, comprises a first step 302, in which a temperature, e.g., a skin temperature, of the occupant is measured. In a second step 304, a core body temperature of the occupant is determined based on the skin temperature. In a third step 306, the core body temperature is associated with a time of day at which the temperature of the occupant was measured. In a fourth step 308, a plurality of recorded core body temperatures and associated times may be processed in order to determine a standard circadian cycle of the core body temperature of the occupant, e.g., a pattern of core body temperature changes during a 24 hour period.

The method 300 may also comprise determining a standard circadian cycle of sleep requirement of the occupant during the 24 hour period. In order to determine the pattern in the occupant's sleep requirement, the occupant's sleep requirement may be estimated based on the time of day when temperature measurements were taken by the vehicle, e.g. the times of day when they are using the vehicle. Additionally or alternatively, the circadian cycle of the occupant's sleep requirement cycle may be fitted to the circadian cycle of the occupant's core body temperature. For example, the cycle of sleep requirement may be determined such that the minimum sleep requirement occurs at substantially the same time as, or shortly after, e.g., 2 or 3 hours after, the core body temperature of the occupant is at a minimum according to the standard circadian cycle. Additionally or alternatively, the cycle of sleep requirement may be determined such that the maximum sleep requirement occurs at substantially the same time as, or shortly after, e.g., 2 or 3 hours after, the core body temperature of the occupant is at a maximum according to the standard circadian cycle.

Using the method 300 described above, the occupant's standard circadian cycle may be determined most accurately for the periods of time in which the occupant regularly uses the vehicle. The standard circadian cycle for period when the occupant does not use the vehicle may be estimated, e.g. using a data model, which may be configured to predict an expected circadian cycle of a person based on one or more core body temperature measurements.

Once the standard circadian cycle of the occupant has been determined by the vehicle, e.g. according to the method 300, it may be possible for the vehicle to identify any deviations in the occupant's position in their standard circadian cycle for the time of day. This may be reflective of the occupant's sleep requirement being greater or less than expected for the current time of day.

As mentioned above, external factors can affect the person's circadian cycle and/or the position of the person on their circadian cycle. Hence, if it is determined that the position of the occupant of the vehicle on their circadian cycle is different from the expected position for the current time of day, it may be desirable to control the environment within the vehicle interior, in order to adjust the position of the occupant on their circadian cycle or compensate for the fact that they are not aligned with their standard circadian cycle.

The environment within the vehicle interior may be controlled such that the environment, e.g., one or more aspects of the environment, experienced by more than one or each of the occupants is controlled separately. However, it will be appreciated that some controls applied to the environment within the vehicle interior will be experienced by each of the occupants. In this case, the environment may be controlled in order compensate for the driver's position on their circadian cycle, e.g., in preference to the other occupants of the vehicle. Alternatively, the environment may be controlled in order compensate for a passenger's position on their circadian cycle. The driver or another occupant may select one of the occupants, e.g. the driver or a passenger, and the environment within the interior of the vehicle may be controlled in order to compensate for the position of the selected occupant on their circadian cycle.

Figure 4:
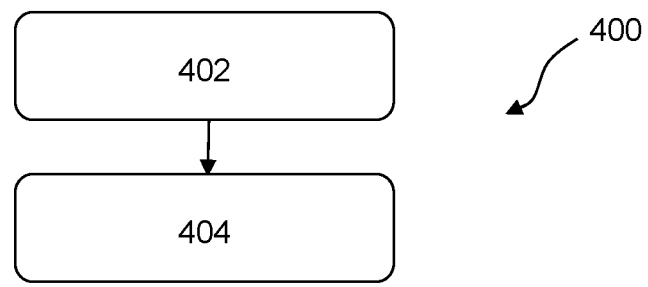
FIG. 4 shows a method of controlling an environmental control system of a motor vehicle according to arrangements of the present disclosure.

With reference to FIG. 4, a method 400 of operating one or more environmental control systems of a vehicle, according to arrangements of the present disclosure comprises a first step 402, in which a position of an occupant of the vehicle on their circadian cycle is determined; and a second step 404, in which the operation of one or more environmental control systems of the vehicle is controlled in order to adjust or compensate for the position of the occupant on their circadian cycle, e.g. compared to their standard circadian cycle.

As described above, in order to determine the occupant's position on their circadian cycle in the first step 402, the occupant's core body temperature may be compared with the standard circadian cycle of the occupant. This may allow a determination to be made of whether the occupant is currently ahead or behind their standard circadian cycle, e.g. for the current time of day.

Once the position of the occupant on their circadian cycle has been determined, the state of other natural processes of the occupant may be determined based on their position on the circadian rhythm. For example, a sleep requirement of the occupant may be determined.

As described with reference to FIG. 1 above, the vehicle 2 comprises the lighting system 8, the media system 10, the climate control system 12 and the air quality system 14. In the second step 404, the operation of one or more of these systems may be controlled in order to affect the environment within the interior 4 of the vehicle 2 and thereby adjust or compensate for the position of the occupant in their circadian cycle, e.g. according to the difference between their current position and their expected position according to the current time of day based on their standard circadian cycle. Their position in their circadian cycle may be adjusted such that it is substantially aligned with their standard circadian cycle.

In one arrangement, the operation of the lighting system 8 may be controlled to adjust the sleep requirement of the occupant. The light received by a person's eyes and/or skin affects how awake or tired they feel, by stimulating or suppressing the formation of melatonin. In particular, the absorption of light towards the blue end of the visible spectrum, e.g., light with a short wavelength, may suppress the formation of melatonin; and the absorption of light towards the red end of the visible spectrum, e.g., light with a low frequency, may enable or stimulate the formation of melatonin in the body. The presence of melatonin may cause a person to advance through their circadian cycle. The magnitude of the effect caused by the light may depend on the intensity or brightness of the light.

The lighting system 8 of the vehicle may therefore be controlled in the second step 502 to provide light of a desirable wavelength and/or intensity in order to adjust or compensate for the position of the occupant in their circadian cycle.

Many people use their vehicles for commuting to a place of work and hence are in their vehicle early in the morning and late in the evening. At these times, the persons may be most susceptible to light therapy. Hence, the use of the lighting system 8 in this way may be particularly beneficial.

Additionally or alternatively, the climate control system 12 of the vehicle may be controlled in order adjust or compensate for the position of the occupant in their circadian cycle. As shown in FIG. 2, core body temperature varies with sleep requirement, such that a person's core body temperature is typically lowest when their sleep requirement is also lowest. A person's core body temperature may increase as they progress through their circadian cycle and their sleep requirement increases. Adjusting the temperature within the vehicle interior may therefore influence the position of the occupant on their circadian rhythm and/or the rate at which they progress through their circadian cycle. Additionally or alternatively, controlling the temperature within the vehicle interior 4 may allow a misalignment between the occupant's position on their circadian cycle and their standard circadian cycle to be compensated for.

For example, if the occupant has a lower than usual core body temperature during their morning commute, increasing the temperature of the vehicle interior may encourage an increase in the occupant's core body temperature, advancing their circadian rhythm and helping them to feel more awake.

In another example, if the occupant has a higher than usual core body temperature later in the day, e.g., in the afternoon or evening, reducing the temperature of the interior of the vehicle may suppress an increase in the occupant's core body temperature, which may prevent the occupant progressing through their circadian cycle, which may lead to the occupant feeling more alert and awake.

Media, such as music, which is being played by the media system 10 of the vehicle 2 may affect how the occupant progresses through their circadian cycle, and/or may affect how tired or awake they feel at a particular point in their circadian cycle. In particular, the volume, tempo and/or equalization of the media may have such an affect.

If the occupant is listening to and/or viewing media using the media system 10, the operation of the media system 10 of the vehicle 2 may be controlled in the second step 404 in order adjust or compensate for the position of the occupant in their circadian cycle.

In some arrangements, the media system 10 may be controlled by directly adjusting the playback of the media. For example, the volume or tempo of the media may be increased or decreased and/or the equalization may be adjusted to increase or decrease the level of bass or treble sound in the media being played.

In other arrangements, the media system 10 may select or schedule media to be played, which has an appropriate tempo and/or equalization according to the position of the occupant on their circadian cycle and/or a difference between their position and their expected position for the time of day.

The quality of air available within the vehicle interior, particularly the levels of oxygen and/or carbon dioxide within the air may also affect how the occupant progresses through their circadian cycle and/or how tired or awake the occupant feels at a particular point in their circadian cycle. Hence, in the second step 404, the operation of an air quality system 14 may be controlled in order to adjust to quality of air within the vehicle interior 4. For example, the air quality system 14 may be controlled to increase the level of oxygen present within the vehicle interior 4. Additionally or alternatively, the air quality system 14 may be controlled to decrease the level of carbon dioxide present within the vehicle interior 4.

As described above, core body temperature of an occupant may provide a good indication of the position of the occupant in their circadian cycle. Additionally or alternatively, an occupant's heart rate may provide an indication or their position in their circadian cycle and/or how quickly they are progressing through their circadian cycle. The vehicle 2 may further comprise a heart rate monitor (not shown) configured to determine a heart rate of the occupant. The position of the occupant on their circadian cycle may be determined at least partially based on the heart rate of the occupant and/or a pattern or rate of change of heart rate over a period.

In some arrangements, the heart rate monitor may be provided within an activity monitor (not shown), which may be configured to be worn or carried by the occupant when they are in the vehicle and/or outside of the vehicle and monitor activities performed by the occupant. For example, the activity monitor may track the occupant's heart rate during performed activities. Additionally or alternatively, the activity tracker may comprise sensors, such as accelerometers, configured to determine a type of activity being performed. The activity monitor may be configured to track the time the occupant spends performing an activity.

The activity monitor may also be configured to determine when the occupant is sleeping and the period of time spent sleeping. The activity monitor may classify the periods of sleep as light sleep and deep sleep.

The vehicle 2, e.g., the controller 20, may be configured to communicate with the activity monitor and receive activity information from the activity monitor. The activity information may relate to the heart rate of the occupant, the type of activities performed by the occupant and the time spent performing each activity. The activity information may also comprise information relating to a period of time the occupant has spent sleeping and the amount of deep and light sleep during that period.

The controller 20 may use the activity information in order to determine a position of the occupant in their circadian rhythm. For example, the controller may refer to the heart rate of the occupant tracked by the activity monitor 18 and may determine how tired the occupant is following activities they have performed, e.g., how much they have progressed though their circadian cycle. The controller 20 may determine, e.g., predict, a position of the occupant on their circadian cycle based on tired the occupant is relative to their standard circadian cycle, e.g., how much their sleep requirement may have increased. When determining how tired the occupant is, the controller 20 may take into account the activities usually performed by the occupant during a 24 hour period, and their heart rate during those activities. The effect of such activities may already be accounted for in the standard circadian cycle determined for the occupant.

The activity information from the activity monitor may allow the controller to determine or improve the standard circadian cycle of the occupant. For example, the vehicle may apply the activity information to determine a standard circadian cycle of sleep requirement of the occupant based on the periods of time the user has spent sleeping. This may allow the accuracy of the standard circadian cycle of core body temperature to be improved by setting the minimum core body temperature according to when the occupant's sleep requirement is smallest, e.g., after the occupant has woken in the morning. For example, the occupant's minimum core body temperature may be set to occur at substantially the same time as, or shortly before, e.g., 2 or 3 hours before, the occupant's sleep requirement is smallest.

When determining the position of an occupant on their circadian rhythm, the controller 20 may consider the period of time the occupant has spent sleeping. For example, if the occupant awoke at an earlier time on a particular day, at a later point during the particular day the controller 20 may determine that the occupant is at a later position in their circadian cycle compared to their standard circadian cycle.

Additionally or alternatively, if the occupant has spent less time sleeping, the controller 20 may determine that the occupant's sleep requirement is greater at a particular point on their circadian cycle compared to their standard circadian cycle.

The controller 20 may be configured to receive calendar information relating to appointments that the occupant has previously attended or is planning to attend. The calendar information may have been entered into, or stored on, a portable computing device, tablet, smart phone, smart watch or other electronic device. The controller 20 may be configured to communicate with the device in order to receive the calendar information.

Additionally or alternatively, the calendar information may be recorded on a networked or online calendar, which may be stored on a networked storage device and/or a cloud storage device accessible via the internet. The vehicle 2, e.g., the controller 20, may be configured to communicate with the networked storage device and/or cloud storage device to receive the calendar information.

The calendar information may comprise information relating to a time of the appointment, a duration of the appointment, a location of the appointment and/or a category of the appointment. The category may indicate whether the appointment is a work appointment, an appointment during which the occupant will be performing an activity, e.g., a physical activity, or an appointment during which the occupant will be resting.

The controller 20 may be configured to determine the standard circadian cycle of the occupant and/or the position of the occupant on their circadian cycle at least partially based on the calendar information. For example, the controller 20 may consider one or more appointments within the calendar information, and may determine a predicted sleep requirement of the occupant based on the timing, length and/or category of the appointments.

The controller 20 may be configured to determine an expected position of the occupant on their circadian cycle at the time of one or more of the appointments, e.g., the planned appointments, and may determine what the occupant's expected sleep requirement will be at the time of the appointments. The controller 20 may be further configured to determine a desirable point in the occupant's circadian cycle for the appointment to be attended. For example, the controller 20 may determine a desirable sleep requirement, e.g., a maximum desirable sleep requirement, for attending the appointment and may determine a desirable point in the circadian cycle based on the desirable sleep requirement.

The controller 20 may be further configured to control the operation of one or more environmental control systems in order to adjust the expected position of the occupant on their circadian cycle at the time of the appointment, such that it is substantially equal to the desirable position in the circadian cycle, e.g., such that the occupant's expected sleep requirement is less than the maximum desirable sleep requirement.

In some cases, it may not be desirable to adjust the expected position of the occupant on their circadian cycle as described above. For example, the adjustment required in order to reach the desired position may be too large and/or may be impractical considering the time of day of the appointment or the time remaining until the appointment. Alternatively, one or more further appointments scheduled at other times may be incompatible with the potential adjustments. In other words, implementing the potential adjustments may result in the further appointments being attended when the occupant is at undesirable positions in their circadian cycle. In this case, the controller 20 may be configured to determine that it is undesirable and/or impractical to adjust the expected position of the occupant on their circadian cycle at the time of the proposed meeting. The controller 20 may be further configured to determine an alternative time to attend the planned appointment, when the occupant would be at a suitable position in their circadian cycle and/or when the occupant's circadian cycle could be suitably adjusted, e.g., through control of the vehicle environmental control systems, such that the occupant is at a suitable position in their circadian cycle at the alternative time. Such an alternative time may be suggested to the occupant.

As mentioned above, the calendar information may include information relating to the location or nature of the appointment, and the controller 20 may determine that one or more of the appointments are to be attended in a location within a different time zone or result in the occupant being in a different time zone. The controller 20 may therefore determine that the occupant is planning to travel to a different time zone. The controller may be configured to determine a desirable circadian rhythm for the occupant based on the difference in time between the different time zone and the time zone of the current location of the vehicle. The controller 20 may be further configured to control the operation of one or more of the environmental control systems to adjust the occupant's position on their circadian cycle to be substantially aligned with or closer to the desirable circadian rhythm.

Similarly, the controller 20 may determine that the occupant has attended a prior appointment at a location in a different time zone to the current location of the vehicle, or that as a result of a prior appointment the occupant has changed time zones, e.g., by travelling from a location in a different time zone to the current location of the vehicle. The controller 20 may therefore determine a jet lag of the occupant based on the difference in time between the time zones. The controller 20 may be further configured to control the operation of one or more of the environmental control systems in order to adjust the occupant's position on their circadian rhythm to be substantially aligned with the occupant's standard circadian cycle, e.g., in order to counteract the effects of jet lag.

It will be appreciated by those skilled in the art that although the invention has been described by way of example, with reference to one or more examples, it is not limited to the disclosed examples and that alternative examples could be constructed without departing from the scope of the invention as defined by the appended claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for operating one or more environmental control systems of a vehicle, the environmental control systems including at least one of a lighting system for providing illumination to an interior of the vehicle, a media system for playing back media within the interior of the vehicle, or an air quality system for controlling an oxygen level within the interior of the vehicle, the method comprising:

determining a circadian cycle position of an occupant of the vehicle;
controlling operation of one or more of the environmental control systems to adjust the circadian cycle position of the occupant, the controlling including one or more of to
  (i) control one or more of color or intensity of the illumination to adjust the circadian cycle position of the occupant,
  (ii) control one or more of volume, tempo or equalization of media played by the media system to adjust the circadian cycle position of the occupant, or
  (iii) control the air quality system to adjust the oxygen level to adjust the circadian cycle position of the occupant;
receiving calendar information relating to an appointment attended or planned by the occupant;
determining a standard circadian cycle of the occupant based at least partially on the calendar information;
determining an expected circadian cycle position of the occupant for a scheduled time of a planned appointment; and
controlling operation of one or more of the environmental control systems to adjust the expected circadian cycle position of the occupant at the scheduled time of the planned appointment.

2. The method of claim 1 further comprising:
determining a core body temperature of the occupant; and
wherein the circadian cycle position of the occupant is determined at least partially based on the core body temperature of the occupant.

3. The method of claim 2, wherein the core body temperature of the occupant is determined based on a skin temperature of the occupant.

4. The method of claim 2 further comprising:
storing the core body temperature of the occupant in a memory associated with the controller;
associating the stored temperatures with a time of day at which the temperature was determined; and
processing the stored temperatures to determine a standard circadian cycle of the occupant.

5. The method of claim 2 further comprising:
determining a sleep requirement of the occupant, at least partially based on the core body temperature of the occupant.

6. The method of claim 5, wherein the sleep requirement of the occupant is at least partially determined by referring the core body temperature of the occupant to a standard circadian cycle of the occupant.

7. The method of claim 6, wherein one or more of the environmental control systems are controlled in order to adjust a circadian cycle position of the occupant to be aligned with the standard circadian cycle of the occupant.

8. The method of claim 1 further comprising:
determining a heart rate of the occupant; and
determining the circadian cycle position of the occupant, at least partially based on the heart rate of the occupant.

9. The method of claim 1 further comprising:
communicating with an activity monitor to receive activity information, the activity monitor worn or carried by the occupant, the activity information being monitored by the activity monitor according to activities performed by the occupant; and
determining a standard circadian cycle of the occupant based at least partially on the activity information.

10. A method for operating one or more environmental control systems of a vehicle, the method comprising:
determining a circadian cycle position of an occupant of the vehicle;
controlling operation of one or more of the environmental control systems to compensate for or adjust the circadian cycle position of the occupant;
receiving calendar information relating to an appointment attended or planned by the occupant;
determining a standard circadian cycle of the occupant based at least partially on the calendar information;
determining an expected circadian cycle position of the occupant for a scheduled time of a planned appointment; and
controlling operation of one or more of the environmental control systems to adjust the expected circadian cycle position of the occupant at the scheduled time of the planned appointment.

11. The method of claim 10 further comprising:
determining an alternative time to perform the planned appointment when the occupant is expected to be at a desired position on their circadian cycle.

12. The method of claim 10 further comprising:
determining a time zone difference expected to be experienced by the occupant based on the planned appointment;
determining a desired circadian rhythm according to the time zone difference; and
controlling operation of one or more of the environmental control systems to adjust the circadian cycle position of the occupant to be aligned with the desired circadian rhythm.

13. The method of claim 10 further comprising:
determining a time zone difference experienced by the occupant based on a previously-attended appointment;
determining a jet lag of the occupant according to the time zone difference; and
controlling operation of one or more of the environmental control systems to adjust the circadian cycle position of the occupant to be aligned with the standard circadian cycle of the occupant.

14. A vehicle, comprising:
one or more environmental control systems, including at least one of a lighting system for providing illumination to an interior of the vehicle, a media system for playing back media within the interior of the vehicle, or an air quality system for controlling an oxygen level within the interior of the vehicle; and
a controller configured to
  determine a circadian cycle position of an occupant of the vehicle,
  control operation of the one or more of the environmental control systems to adjust the circadian cycle position of the occupant, including one or more of to
    (i) control one or more of color or intensity of the illumination to adjust the circadian cycle position of the occupant,
    (ii) control one or more of volume, tempo or equalization of media played by the media system to adjust the circadian cycle position of the occupant, or
    (iii) control the air quality system to adjust the oxygen level to adjust the circadian cycle position of the occupant,
  receive calendar information relating to an appointment attended or planned by the occupant,
  determine a standard circadian cycle of the occupant based at least partially on the calendar information, determine an expected circadian cycle position of the occupant for a scheduled time of a planned appointment, and control operation of one or more of the environmental control systems to adjust the expected circadian cycle position of the occupant at the scheduled time of the planned appointment.

15. The vehicle of claim 14, further comprising:

an infra-red thermometer configured to determine a temperature of the occupant at or close to a central region of a forehead or temple region of the occupant; and wherein the controller is further configured to determine the circadian cycle position of the occupant, at least partially based on a core body temperature of the occupant identified according to data received from the thermometer.

16. The vehicle of claim 14, wherein the environmental control systems include at least two of the lighting system the media system, or the air quality system; and the controller is further configured to at least two of (i) control one or more of color or intensity of the illumination to adjust the circadian cycle position of the occupant, (ii) control one or more of volume, tempo or equalization of media played by the media system to adjust the circadian cycle position of the occupant, or (iii) control the air quality system to adjust the oxygen level to adjust the circadian cycle position of the occupant.

* * * * *